United States Patent [19]

Brunner et al.

[11] 4,287,379

[45] Sep. 1, 1981

[54] PROCESS FOR OBTAINING ISOBUTENE FROM C₄-HYDROCARBON MIXTURES CONTAINING ISOBUTENE

[75] Inventors: Erwin Brunner; Eckart Schubert, both of Ludwigshafen; Alfred Lindner, Bobenheim-Roxheim; Franz Merger; Klaus Volkamer, both of Frankenthal; Max Strohmeyer, Limburgerhof; Gerhard Sandrock, Frankenthal, all of Fed. Rep. of Germany

[73] Assignee: BASF Aktiengesellschaft, Fed. Rep. of Germany

[21] Appl. No.: 137,750

[22] Filed: Apr. 7, 1980

Related U.S. Application Data

[63] Continuation-in-part of Ser. No. 116,554, Jan. 29, 1980, abandoned, which is a continuation of Ser. No. 1,294, Dec. 29, 1978, abandoned.

[30] Foreign Application Priority Data

Jan. 19, 1978 [DE] Fed. Rep. of Germany ....... 2802198

[51] Int. Cl.³ ............................................. C07C 7/00
[52] U.S. Cl. ................................ 585/839; 568/697; 585/864
[58] Field of Search ................ 568/697; 585/864, 839

[56] References Cited

U.S. PATENT DOCUMENTS

| | | | |
|---|---|---|---|
| 3,121,124 | 2/1964 | Verdol | 260/677 |
| 3,170,000 | 2/1965 | Verdol | 568/697 |
| 3,288,842 | 11/1966 | Verdol | 568/697 |
| 3,629,478 | 12/1971 | Haunschild | 260/677 A |
| 3,637,889 | 1/1972 | Watanabe et al. | 260/682 |
| 4,020,114 | 4/1977 | Rescali et al. | 260/681.5 R |
| 4,039,590 | 8/1977 | Ancillotti et al. | 260/614 R |
| 4,071,567 | 1/1978 | Ancillotti et al. | 260/680 R |

FOREIGN PATENT DOCUMENTS

2229769  1/1978  Fed. Rep. of Germany.

OTHER PUBLICATIONS

Perry et al. Chemical Engineers Handbook 5th ed. (1976), pp. 13-36.

*Primary Examiner*—Arthur P. Demers
*Attorney, Agent, or Firm*—Keil & Witherspoon

[57] ABSTRACT

A process for obtaining isobutene from a C₄-hydrocarbon mixture containing isobutene, by reacting the mixture with a primary alcohol in the presence of an acid condensing agent and decomposing the resulting tertiary ether in the presence of an acid catalyst at an elevated temperature, wherein a primary C₃- or C₄-alcohol is used.

12 Claims, 1 Drawing Figure

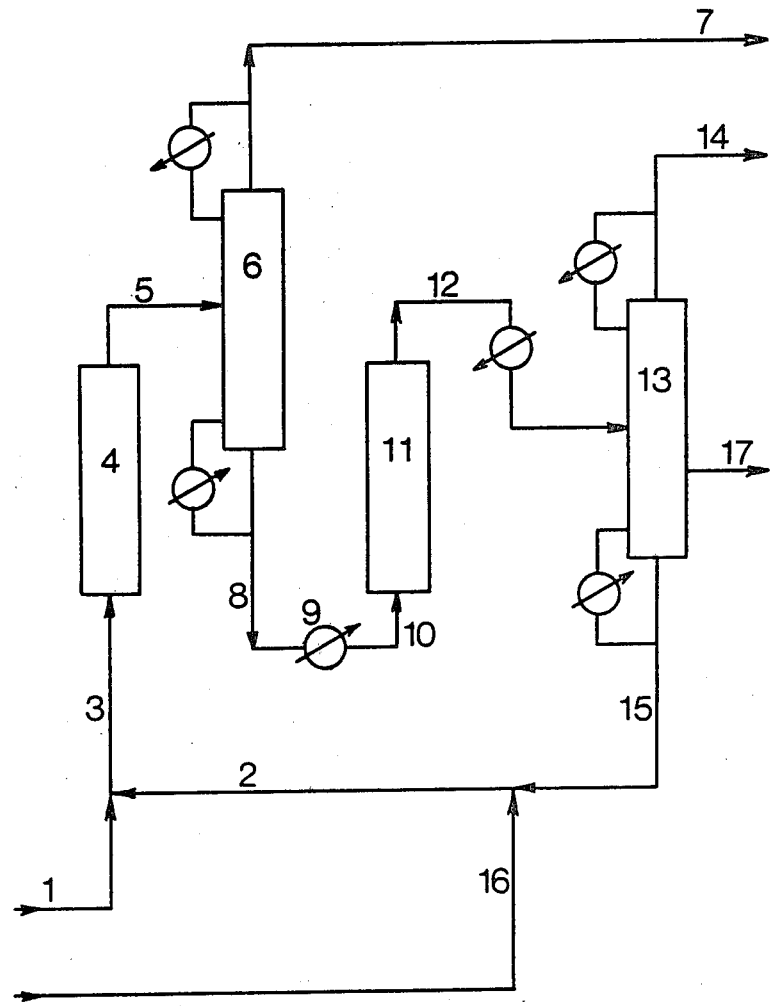

PROCESS FOR OBTAINING ISOBUTENE FROM C$_4$-HYDROCARBON MIXTURES CONTAINING ISOBUTENE

REFERENCE TO RELATED APPLICATIONS

This application is a continuation-in-part of our co-pending application Ser. No. 116,554, filed Jan. 29, 1980, now abandoned, which in turn is a continuation of application Ser. No. 1,294 filed Dec. 29, 1978, now abandoned.

BACKGROUND AND SUMMARY OF THE INVENTION

The present invention relates to a process for obtaining isobutene from a C$_4$-hydrocarbon mixture containing isobutene, by reacting the mixture with a primary C$_3$- or C$_4$-alcohol, isolating the tertiary ether formed and decomposing it at an elevated temperature.

It is already known to obtain isobutene from a C$_4$-hydrocarbon mixture by means of a sulfuric acid extraction process. In this process, highly concentrated sulfuric acid must be used and consequently expensive materials must be employed for the equipment. Since, furthermore, side-reactions of isobutene, for example dimerization, polymerization, hydration and the like, occur during the extraction, the sulfuric acid extraction process is not satisfactory in respect of yield, and of quality of the products.

A process for obtaining isobutene is also known, for example from German Pat. No. 1,216,865 or German Published Applications DAS No. 1,934,422 and DAS No. 2,011,826, in which a C$_4$-hydrocarbon mixture containing isobutene is reacted with methanol in a first stage and the resulting methyl tert-butyl ether is decomposed into methanol and isobutene in a second stage. However, the known processes have the disadvantage that methanol forms azeotropic mixtures with the C$_4$-hydrocarbons. For example it is known from German Laid-Open Application DOS No. 2,629,769 and German Published Application DAS No. 1,934,422 that in the preparation of methyl tert-butyl ether, when the unconverted hydrocarbons are removed from the reaction mixture by distillation they contain about 2% of methanol, due to the hydrocarbon/methanol azeotropes, and this methanol can only be recovered by expensive methods, for example by interpolating a water wash. It is a particular disadvantage that on separating by distillation the reaction mixture obtained from the decomposition stage and containing isobutene and methanol, the methanol and isobutene form an azeotropic mixture so that an expensive water wash must also be interpolated into the decomposition stage (cf., for example, German Published Application DAS No. 1,934,422) in order to minimize the loss of methanol and obtain a methanol-free isobutene, as is required for most applications.

It is true that in addition to the use of methanol and possibly ethanol as alcohols for the etherification reaction, primary alcohols in general have previously been referred to as possible reactants for the conversion to the tertiary ether (cf., for example, German Pat. No. 1,216,865 and German Published Applications DAS Nos. 1,934,422 and 2,011,826, already referred above). However, there was a substantial prejudice against the use of higher primary alcohols, for example C$_3$- or C$_4$-alcohols, since it was known that such higher primary alcohols can easily be dehydrated to undesired olefins under the reaction conditions of the decomposition stage, in the presence of an acid catalyst. For example, German Published Application DAS No. 1,934,422, already referred to, expressly points out, in column 3, 1st paragraph, that methanol, which cannot be dehydrated, should be used as the alcohol in order to avoid the undesirable formation of olefins in the decomposition stage.

A further substantial prejudice against the use of higher primary alcohols resulted from the fact that it was known, for example from U.S. Pat. No. 3,170,000, especially Table I and column 3, lines 29 to 31 that methanol and ethanol give substantially higher yields in the etherification reaction than do the higher primary alcohols, e.g., the C$_3$- or C$_4$-alcohols.

Because of the disadvantages and prejudices described above, the conventional processes for obtaining isobutene by decomposing the tertiary ether obtained in a first etherification stage have not found industrial use but have only remained prior art on paper, and hence the industrial production of isobutene had to depend on the use of the sulfuric acid extraction process, with all the shortcomings and disadvantages inherent in the said process.

In is an object of the present invention to provide a process for obtaining isobutene from a C$_4$-hydrocarbon mixture containing isobutene, which does not suffer from the disadvantages of the conventional processes.

We have found that this object is achieved by a simple process for obtaining isobutene from a C$_4$-hydrocarbon mixture containing isobutene, by reacting the mixture with a primary alcohol in the presence of an acid condensing agent and decomposing the resulting tertiary ether in the presence of an acid catalyst at an elevated temperature, wherein the primary alcohol used is a primary C$_3$- or C$_4$-alcohol and the acid condensing agent used for the formation of the ether is an ion exchanger in its acid form, and the primary C$_3$- or C$_4$-alcohol and the C$_4$-hydrocarbon mixture are fed, with or without prior mixing, first to the etherification reaction zone, which contains the ion exchanger, the reaction mixture obtained from the etherification reaction zone is then distilled in a first distillation zone, in which the top product, taken off without interpolating a water wash, is a C$_4$-hydrocarbon mixture comprising the unconverted hydrocarbons and containing not more than 1,000 ppm by weight of primary C$_3$- or C$_4$-alcohol, and the bottom product taken off is the resulting C$_3$- or C$_4$-alkyl tert-butyl ether, which may contain primary C$_3$- or C$_4$-alcohol which may have been added in excess, the bottom product is then fed to a second reaction zone, containing an acid catalyst, in which the C$_3$- or C$_4$-alkyl tert-butyl ether is decomposed at an elevated temperature to give isobutene and primary C$_3$- or C$_4$-alcohol, the mixture of isobutene and primary C$_3$- or C$_4$-alcohol is fed to a second distillation zone in which isobutene containing not more than 500 ppm by weight of primary C$_3$- or C$_4$-alcohol is taken off as the top product without interpolating a water wash and the primary C$_3$- or C$_4$-alcohol is taken off as the bottom product, and the resulting primary C$_3$- or C$_4$-alcohol is recycled to the etherification reaction zone.

Using the novel process, a C$_4$-hydrocarbon raffinate which is virtually free from C$_3$- or C$_4$-alcohol is isolated from the reaction mixture obtained after the etherification stage, by simple distillation without interpolating a water wash, since unconverted primary C$_3$- or C$_4$- alcohol surprisingly does not form an azeotrope with the C$_4$-hydrocarbons. In general, a C$_4$-hydrocarbon raffinate containing not more than 1,000 ppm by weight of C$_3$- or C$_4$-alcohol, preferably at most 500 ppm by weight, in particular at most 100 ppm by weight, is taken off as the top product of the distillation. Again, when the reaction mixture, obtained on decomposing the C$_3$- or C$_4$-alkyl tert-butyl ether, is separated by distillation into isobutene and the C$_3$- or C$_4$-alcohol, azeotropes of the alcohol are not formed. The C$_3$- or C$_4$-alcohol can therefore be recovered, without interpolation of a water wash, in a simple manner and virtually without losses, and be recycled to the etherification stage.

Surprisingly, the process according to the invention gives isobutene in high yield, for example in a yield of more than 97%, based on the isobutene contained in the C$_4$-hydrocarbon mixture employed. This was unexpected since U.S. Pat. No. 3,170,000, already referred to, states in column 3 that on using C$_3$- or C$_4$-alcohols only very poor yields of tertiary ether are obtained. It is also known from U.S. Pat. No. 3,634,535, especially column 6, that the reaction of isobutene with propanol gives the tertiary ether in a yield of only about 50%, whilst the corresponding reaction of isobutene and methanol gives yields of from about 90 to 95%. It is therefore surprising that yields of tertiary ether of more than 95% are obtained by the process according to the invention.

BRIEF DESCRIPTION OF THE DRAWING

The single FIGURE shows an illustrative embodiment of the process according to the invention in schematic form.

DETAILED DESCRIPTION OF THE INVENTION

Isobutene-containing C$_4$-hydrocarbon mixtures suitable for the process of the invention are obtained, for example, from the thermal or catalytic cracking of petroleum products, from the manufacture of ethylene by pyrolysis of liquefied petroleum gas (LPG), naphtha, gas oil or the like, or from the catalytic dehydrogenation of n-butane and/or n-butene. These C$_4$-hydrocarbon mixtures as a rule contain olefinic and paraffinic C$_4$-hydrocarbons in addition to the isobutene and may also contain butadiene, for example in amounts of up to 70 percent by weight, and higher acetylenes, e.g., but-1-yne and butenyne. Butadiene-containing C$_4$-hydrocarbon mixtures may be employed as such or after first removing the butadiene from the C$_4$-hydrocarbon mixture, for example by extraction with a selective solvent. The C$_4$-hydrocarbon mixtures may in addition contain C$_3$-hydrocarbons, e.g., propane, propene and propyne, for example in amounts of up to 10 percent by weight. In general, the C$_4$-hydrocarbon mixtures contain from 5 to 95 percent by weight, preferably from 10 to 90 percent by weight, in particular from 20 to 70 percent by weight, of isobutene. Preferably, C$_4$-hydrocarbon mixtures are used which in addition to isobutene contain n-butane, isobutane, but-1-ene, trans-but-2-ene and cis-but-2-ene, with or without buta-1,3-diene.

The primary C$_3$- or C$_4$-alcohols (i.e. alcohols of 3 or 4 carbon atoms) to be used according to the invention are in general n-propanol, n-butanol or isobutanol, preferably n-propanol or isobutanol, and especially isobutanol. The alcohols are used, for example, as technical-grade products of conventional purity, for example of a purity of at least 95%, preferably at least 98%.

The acid condensing agents used for the etherification which represents the first stage are ion exchangers in the acid form. Examples of suitable ion exchangers are sulfonated coal, sulfonated phenol-formaldehyde resins, sulfonated resins derived from coumarone-indene condensation products and, in particular, sulfonated polystyrene resins, e.g. nuclear-sulfonated cross-linked styrene-divinylbenzene copolymers. The amount of the ion exchanger is in general from 0.01 to 1 liter of bulk volume per liter of reactor volume. The ion exchangers may be used as such or on a carrier. Examples of suitable carriers are alumina, silica, active charcoal and plastics, e.g., styrene polymers. The etherification may be carried out in, for example, stirred kettles or fixed bed reactors, the latter being preferred.

A particularly advantageous method of carrying out the etherification is such that the exit temperature of the reaction mixture from the etherification zone is from 25° to 65° C., preferably from 30° to 60° C., especially from 30° to 50° C. Preferably, exit temperatures which are lower than the mean temperature in the etherification stage are employed. In general, the etherification reaction results is not less than 90%, preferably not less than 95%, in particular not less than 96%, conversion of the isobutene, contained in the C$_4$-hydrocarbon mixture, to the C$_3$- or C$_4$-alkyl tert-butyl ether.

The etherification according to the invention can be carried out under atmospheric pressure. However, it is advantageous to work under slightly superatmospheric pressure, for example at from 1.01 to 30 bar, especially from 2 to 20 bar. The isobutene-containing C$_4$-hydrocarbon mixture can, depending on the pressure and temperature, be employed for the reaction as a liquid or a gas. Preferably, liquid isobutene-containing C$_4$-hydrocarbon mixtures are employed. The etherification can be carried out batchwise. In that case, the reaction times are in general from 1 minute to 5 hours. Preferably, however, the etherification is carried out continuously, in which case the quotient of the volume of the reaction zone (in volume units) and the throughput in volume units per hour is in general from 0.01 to 5 hours, preferably from 0.02 to 1 hour, especially from 0.03 to 1 hour.

For the etherification reaction, the weight ratio of primary C$_3$- or C$_4$-alcohol to the isobutene contained in the C$_4$-hydrocarbon mixture is in general from 100:1 to 1:1, preferably from 20:1 to 1.2:1, especially from 4:1 to 1.3:1.

The reaction mixture which is obtained from the etherification reaction zone and which as a rule still contains excess primary C$_3$- or C$_4$-alcohol which had been added for the etherification reaction is separated by distillation, without interpolating water wash, and the top product taken off is a C$_4$-hydrocarbon raffinate substantially free from isobutene, the isobutene content in general being not more than 5 percent by weight, preferably not more than 2.5 percent by weight, especially not more than 1.5 percent by weight. Preferably, the top product taken off is a C$_4$-hydrocarbon raffinate containing not more than 200 ppm by weight of C$_3$- or C$_4$- alkyl tert-butyl ether and/or di-C$_3$-alkyl or di-C$_4$-alkyl ether.

The bottom product from the distillation of the reaction mixture obtained after the etherification consists of the C$_3$- or C$_4$-alkyl tert-butyl ether which may or may not still contain excess primary C$_3$- or C$_4$-alcohol. Advantageously, a bottom product containing not more than 1,000 ppm by weight, preferably not more than 500 ppm by weight, especially not more than 100 ppm by weight, of $C_4$-hydrocarbons is taken off.

Thereafter, in the second stage of the process, the tertiary ether obtained is decomposed into isobutene and primary $C_3$- or $C_4$-alcohol in the presence of an acid catalyst at elevated temperatures. The starting material of the decomposition can be a tertiary ether which is virtually free from $C_3$- or $C_4$-alcohol and which has been obtained, for example, by using, for the etherification, an amount of $C_3$- or $C_4$-alcohol corresponding to at most the stoichiometrically required amount of alcohol, or by removing (for example by distillation) excess added primary $C_3$- or $C_4$-alcohol from the bottom product obtained after distillation of the etherification reaction mixture. Preferably, however, the tertiary ether obtained as the bottom product after removing the $C_4$-hydrocarbon raffinate by distillation is employed for the decomposition without further removal of any excess $C_3$- or $C_4$-alcohol which may be present. Alternatively, it is also possible to remove only a part of the excess $C_3$- or $C_4$-alcohol. In general, the $C_3$- or $C_4$-alkyl tert-butyl ether formed is used in the decomposition stage without addition of water.

To carry out the decomposition, the tertiary ether is vaporized and brought into contact with the acid catalyst in the vapor phase. Examples of suitable acid catalysts are ion exchangers in the acid form, e.g., sulfonated coal, sulfonated phenol-formaldehyde resins, sulfonated resins derived from coumarone-indene condensation products and, in particular, sulfonated polystyrene resins, e.g., nuclearsulfonated, crosslinked styrene-divinylbenzene copolymers.

Other catalysts which may be used advantageously are solid phosphoric acid catalysts which comprise monophosphoric acid or preferably polyphosphoric acid on a solid carrier. Examples of suitable carriers for the phosphoric acid catalysts are alumina, silica, active charcoal, kieselguhr or pumice. Silica gel is the preferred carrier.

Other suitable acid catalysts are metal sulfates, e.g., sodium bisulfate, calcium bisulfate, aluminum sulfates, nickel sulfate, copper sulfate, cobalt sulfate, cadmium sulfate and strontium sulfate. These sulfates may be used unsupported but are preferably used on a carrier. Examples of suitable carriers are silica gel, active charcoal, alumina and pumice.

Further suitable catalysts for the decomposition are silica gel or alumina used by themselves.

In a further embodiment of the process according to the invention, a metal phosphate, especially a metal hydrogen phosphate, is used as the acid decomposition catalyst. These phosphates may also contain phosphoric acid in excess over the amount corresponding to the stoichiometric composition of the acid metal phosphate, for example in an excess of up to 65%, preferably from 1 to 50%, in particular from 10 to 20%. Examples of such metal phosphates are magnesium phosphates, calcium phosphates, strontium phosphates, barium phosphates, manganese phosphates, nickel phosphates, copper phosphates, cobalt phosphates, cadmium phosphates, iron (II) phosphates, chromium phosphates and in particular aluminum phosphates. The metal phosphate catalyst can be used as such or on a carrier. Examples of suitable carriers are alumina, silica, active charcoal and zinc oxide.

The amount of the acid catalyst is in general from about 0.01 to 1 kg, preferably from about 0.03 to 0.3 kg, per kg of tertiary ether passed through the reactor per hour. Preferably, fixed bed reactors are used for the decomposition of the tertiary ether.

The decomposition temperature of the tertiary ether varies with the nature of the acid catalyst and with the contact time, but is in general from 50° to 350° C., preferably from 80° to 300° C., in particular from 100° to 250° C. If a metal phosphate or phosphoric acid catalyst is used as the decomposition catalyst, the decomposition is in general carried out at from 80° to 350° C., preferably from 90° to 260° C., especially from 170° to 210° C.

The contact time of the vaporized tertiary ether is advantageously from 0.1 to 20 seconds, preferably from 1 to 10 seconds.

The decomposition of the tertiary ether can be carried out under atmospheric pressure, but is in general carried out under superatmospheric pressure, for example at up to 30 bar, preferably up to 20 bar. Advantageously, the decomposition of the tertiary ether is carried out under pressures of from 2 to 15 bar, preferably from 3 to 12 bar, especially from 4 to 12 bar. However, the decomposition can also be carried out under reduced pressure.

The decomposition of the tertiary ether may be carried out batchwise but is preferably carried out continuously.

The reaction mixture obtained from the decomposition, which contains isobutene and primary $C_3$- or $C_4$-alcohol as the reaction products, is fed to a second distillation zone, in which isobutene containing not more than 500, preferably not more than 100, especially not more than 50, ppm by weight of primary $C_3$- or $C_4$-alcohol is taken off as the top product, without interpolating a water wash. Advantageously, a top product which is not less than 99.3% by weight pure, preferably not less than 99.5% by weight pure, especially not less than 99.7% by weight pure, and which contains the di-$C_3$-alkyl ether or di-$C_4$-alkyl ether, which may be formed in very small amounts as a by-product, and/or the $C_3$- or $C_4$-alkyl tert-butyl ether, in an amount of at most 100 ppm by weight, preferably at most 50 ppm by weight, especially at most 20 ppm by weight, is taken off. The primary $C_3$- or $C_4$-alcohol obtained as the bottom product from the second distillation zone is recycled to the etherification reaction zone. Preferably, the content of di-$C_3$-alkyl ether or di-$C_4$-alkyl ether, which may be formed in very small amounts as a by-product but accumulates in the recycled primary $C_3$- or $C_4$-alcohol, is restricted to from 2 to 20% by weight in the latter.

In the novel process, it can be advantageous, if isobutanol is used as the $C_4$-alcohol, to bleed off a part of the stream of isobutanol in order to remove any impurities which may have accumulated, in which case the bleed-stream is advantageously taken from the side of the second distillation zone, or from the bottom product taken off the second distillation zone. Advantageously, the isobutanol bleed-stream is in general from 0.1 to 10% by weight, preferably from 0.5 to 5% by weight, of the total isobutanol stream. The isobutanol bleed-stream taken off to remove any diisobutyl ether formed advantageously contains from 3 to 40% by weight, preferably from 5 to 35% by weight, especially from 10 to 30% by weight, of diisobutyl ether.

In an advantageous embodiment of the process, the isobutanol bleed-stream is dehydrated in the conventional manner in the presence of a dehydrating catalyst, resulting in the dehydration of not only the isobutanol but also the diisobutyl ether, and thereby additionally increasing the yield of isobutene.

Advantageously, the dehydration is carried out in the gas phase over a catalyst. Examples of suitable catalysts are silica gel, thorium oxide, titanium (IV) oxide and especially alumina. In general, the dehydration is carried out at from 250° to 450° C., preferably from 300° to 400° C. It can be advantageous to carry out the dehydration in the presence of water, which may or may not be added for the purpose.

As indicated in the drawing, the isobutene-containing $C_4$-hydrocarbon mixture (fed through line 1) and the primary $C_3$- or $C_4$-alcohol (fed through line 2) are mixed, and the resulting mixture is passed through line 3 to the etherification reaction 4, which contains the ion exchanger. Advantageously, the reactor is a fixed bed reactor, e.g., a flow tube or a loop reactor or a combination of both types. However, other types of reactor, for example a stirred kettle or a stirred kettle cascade, can also be used. The reaction mixture obtained is taken from the reactor through line 5 and fed to a first distillation column 6. At the top of the distillation column, substantially isobutene-free $C_4$-hydrocarbon raffinate is taken off through line 7. The tertiary ether which is obtained as the bottom product of the distillation column 6 and which may contain excess primary $C_3$- or $C_4$-alcohol is next fed to the vaporizer 9 through line 8, and after vaporization is passed through line 10 into the reactor 11 which contains the acid catalyst. This reactor is in general a fixed bed reactor. The mixture of isobutene and primary $C_3$- or $C_4$-alcohol taken from reactor 11 is passed through line 12 into the distillation column 13 where very pure isobutene is obtained as the top product, which is taken off through line 14. The $C_3$- or $C_4$-alcohol obtained as the bottom product is returned to the etherification reactor 4 through lines 15 and 2, where necessary after replenishing the $C_3$- or $C_4$-alcohol through line 16. Advantageously, a small bleed-stream containing $C_3$- or $C_4$-alcohol is taken off through line 17 to remove any impurities formed, e.g., diisobutyl ether, diisobutene or triisobutene. If isobutanol is used as the $C_3$- or $C_4$-alcohol, this bleed-stream can be fed to a dehydration reactor, where additional isobutene is obtained.

Using the process according to the invention, very pure isobutene is obtained, which in particular is suitable for the manufacture of high molecular weight polymers of isobutene.

The Examples which follow illustrate the invention.

EXAMPLE 1

The etherification was carried out using a $C_4$-hydrocarbon mixture which consisted to the residue (raffinate) of a $C_4$-fraction, obtained from an ethylene production installation, from which the butadiene has been extracted. After the extraction of the butadiene, the $C_4$-hydrocarbon mixture had the following composition:

| | |
|---|---|
| isobutane | 1.9% by volume |
| n-butane | 8.1% by volume |
| isobutene | 46.0% by volume |
| but-1-ene | 26.7% by volume |
| trans-but-2-ene | 10.0% by volume |
| cis-but-2-ene | 7.0% by volume |
| buta-1,3-diene | 0.2% by volume |

Per hour, a mixture of 258 g of this $C_4$-hydrocarbon mixture and 320 ml of isobutanol was introduced into a stainless steel tubular reaction vessel which contained 254 ml of a sulfonated styrene-divinylbenzene copolymer resin in the acid form (Lewatit SPC 118, particle size 0.8–1 mm). A temperature of 40° C. and a pressure of 12 bar were maintained in the reaction vessel. The reaction mixture obtained was fed to a distillation column, and at the top of the column a butene/butane raffinate containing less than 2 percent by weight of isobutene was obtained. The raffinate was virtually free from isobutanol and could therefore be used directly, without additional purification operations (for example without interpolation of a water wash), as the starting material for further reactions. At the bottom of the column, 500 ml per hour of isobutyl tert-butyl ether, which still contained 24.3 percent by weight, based on the mixture, of excess isobutanol, were taken off and fed to a vaporizer. The vaporized isobutyl tert-butyl ether, heated to 190° C., was cracked by passing it into a tubular cracking reactor which contained phosphoric acid on silica (20% excess of phosphoric acid) as the cracking catalyst; cracking took place at 190° C., giving isobutene and isobutanol. The cracked reaction product was passed into a second distillation column, at the top of which 115 g per hour of very pure isobutene of the following composition were obtained:

| | |
|---|---|
| isobutene | 99.85% by weight |
| isobutane | 730 ppm by weight |
| butane | 3 ppm by weight |
| but-1-ene | 420 ppm by weight |
| trans-but-2-ene | 190 ppm by weight |
| cis-but-2-ene | 160 ppm by weight |
| buta-1,3-diene | 19 ppm by weight |

The yield of isobutene, based on isobutene originally contained in the $C_4$-hydrocarbon mixture employed, was 97.7%. At the bottom of the second distillation column, 320 ml per hour of isobutanol were obtained, and this material was recycled to the etherification reaction.

It proved possible to effect a 4-fold increase in the throughput of $C_4$-hydrocarbon mixture and isobutanol through the etherification reactor, with virtually no change in the purity of the butene/butane raffinate obtained on distillation, and of the product, containing isobutyl tert-butyl ether, obtained at the bottom of the distillation column.

COMPARATIVE EXAMPLE 1

The etherification was carried out as described in Example 1, at 40° C., but employing the corresponding stoichiometric amount of methanol instead of isobutanol. With a throughput, of starting mixture, of 2 liters/h per liter of reactor volume, the residual content of isobutene in the butene/butane raffinate obtained after distillation was more than 30 percent by weight. In addition, this raffinate contained more than 1.5 mole % of methanol, which was washed out of the raffinate by treatment with water. The methanol was recovered from the methanol-water mixture obtained after the water wash, and was recycled to the etherification reaction. The butene/butane raffinate was then dried in order to remove the entrained water.

By contrast, when using isobutanol (as described in Example 1) instead of methanol, a butene/butane raffinate containing less than 1 ppm of isobutanol is obtained by simple distillation.

COMPARATIVE EXAMPLE 2

The ether cleavage was carried out as described in Example 1, but instead of isobutyl-tert-butyl ether, methyl tert-butyl ether was used. Impure isobutene having the following composition was obtained at the top of the distillation column:

| | |
|---|---|
| isobutene | 97.0% by weight |
| other hydrocarbons | 0.15% by weight |
| methanol | 2.45% by weight |
| dimethyl ether | 0.4% by weight |

The isobutene obtained contained 2.45% by weight of methanol and, in addition, 0.4% by weight of dimethyl ether, whilst in the isobutene obtained according to Example 1 the content of isobutanol and of diisobutyl ether was below the limit of detectability (4 ppm).

For many applications, for example for use as a starting material for cationic polymerization with boron fluoride, the isobutene obtained in the Comparative Example must be subjected to additional purification operations, whereas the very pure isobutene obtained according to Example 1 can be employed directly. In order to obtain, from the isobutene produced in Comparative Example 2, an isobutene of similar purity to that obtained in Example 1, it would be necessary according to the prior art, to carry out the following typical additional process steps.

(1) Distillation of the isobutene to remove the dimethyl ether;

(2) Subsequent extraction of the isobutene with water to remove methanol;

(3) Drying the resulting moist isobutene;

(4) Distillation of the methanol-water mixture, obtained from the extraction in order to recover the methanol.

EXAMPLE 2

The etherification was carried out using the $C_4$-cut from an ethylene production installation. The $C_4$-hydrocarbon mixture had the following composition:

| | |
|---|---|
| butane | 3.65% by weight |
| isobutane | 1.41% by weight |
| but-1-ene | 20.44% by weight |
| isobutene | 23.52% by weight |
| trans-but-2-ene | 4.95% by weight |
| cis-but-2-ene | 3.15% by weight |
| buta-1,3-diene | 42.31% by weight |
| buta-1,2-diene | 0.10% by weight |
| but-1-yne | 0.11% by weight |
| butenyne | 0.36% by weight |

Per hour, a mixture of 457 g of this hydrocarbon cut and 320 ml of isobutanol was reacted as described in Example 1. The isobutene content of the butene/butane raffinate obtained after distillation was 1.0 percent by weight.

The bottom product from the first distillation was vaporized and then passed into a tubular cracking reactor, where the isobutyl tert-butyl ether was cracked, at 190° C., to give isobutene and isobutanol. The isobutene (107 g per hour) taken off at the top of the downstream distillation stage had the following composition:

| | |
|---|---|
| butane | 0.012% by weight |
| isobutane | 0.041% by weight |
| but-1-ene | 0.042% by weight |
| isobutene | 99.332% by weight |
| trans-but-2-ene | 0.09% by weight |
| cis-but-2-ene | 0.11% by weight |
| buta-1,3-diene | 0.36% by weight |
| buta-1,2-diene | 0.007% by weight |
| but-1-yne | 0.0032% by weight |
| butenyne | 0.0028% by weight |

In spite of the $C_4$-hydrocarbon mixture used as the starting material having a buta-1,3-diene content of 42.31 percent by weight, the content of buta-1,3-diene in the isobutene product was only 0.36 percent by weight. Equally, the concentrations of buta-1,2-diene, but-1-yne and butenyne were greatly reduced.

The yield of isobutene, based on isobutene contained in the $C_4$-hydrocarbon mixture employed, was 96.5%. The isobutanol, which was recovered virtually completely from the bottom of the second distillation column, was recycled to the etherification reaction.

EXAMPLE 3

The etherification was carried out using a $C_4$-hydrocarbon mixture which consisted of the residue (raffinate) of a $C_4$-fraction, obtained from an ethylene production installation, from which the butadiene had been extracted. After the extraction of the butadiene, the $C_4$-hydrocarbon mixture had the following composition:

| | |
|---|---|
| isobutane | 1.9% by volume |
| n-butane | 8.1% by volume |
| isobutene | 46.0% by volume |
| but-1-ene | 26.7% by volume |
| trans-but-2-ene | 10.1% by volume |
| cis-but-2-ene | 7.0% by volume |
| butadiene | 0.2% by volume |

Per hour, a mixture of 250 g of this $C_4$-hydrocarbon mixture and 266 ml of n-propanol was introduced into a stainless steel tubular reaction vessel which contained 138 ml of a sulfonated styrene-divinylbenzene copolymer resin in the acid form (Lewatit SPC 118, particle size 0.8–1 mm). A temperature of 40° C. and a pressure of 12 bar were maintained in the reaction vessel. The reaction mixture obtained was fed to a distillation column, and at the top of the column a butene/butane raffinate containing 2 percent by weight of isobutene was obtained. The raffinate was virtually free from propanol and could therefore be used directly, without additional purification operations (for example without interpolation of a water wash), as the starting material for further reactions. At the bottom of the distillation column, 428 ml per hour of propyl tert-butyl ether, which still contained 27 percent by weight, based on the mixture, of excess propanol, were taken off and fed to a vaporizer. The vaporized propyl tert-butyl ether, heated to 170° C. was cracked by passing it into a tubular cracking reactor which contained 20% of $H_3PO_4$ on heat-treated silica gel as the cracking catalyst; cracking took place at from 180° to 200° C. giving isobutene and propanol. The cracked reaction product was passed into a second distillation column, at the top of which 95.7 g per hour of very pure isobutene of the following composition were obtained:

| | |
|---|---|
| isobutene | 99.9% by weight |
| isobutane | 300 ppm by weight |
| butane | 100 ppm by weight |
| but-1-ene | 100 ppm by weight |
| trans-but-2-ene | 100 ppm by weight |
| cis-but-2-ene | 100 ppm by weight |
| buta-1,3-diene | 100 ppm by weight |

At the bottom of the second distillation column, 287 ml per hour of propanol, containing 7.2% of propyl tert-butyl ether, were obtained. It was possible to recycle this mixture to the etherification reaction, whereby the amount of isobutene obtained could be increased to 112 g per hour.

The yield of isobutene, based on isobutene contained in the $C_4$-hydrocarbon mixture employed, was 97.5% if the entire bottom product was recycled to the second distillation column.

The foregoing description of the invention has been directed to particular embodiments in accordance with the requirements of the Patent Act and for the purposes of explanation and illustration. It will be apparent, to those skilled in this art that many modifications and changes in both apparatus and process may be made without departing from the scope and spirit of our invention. It is our intension in the following claims to cover all such equivalent modifications and variations as fall within the true scope and spirit of our invention as disclosed herein.

We claim:

1. A process for obtaining isobutene from a $C_4$-hydrocarbon mixture containing isobutene, which comprises
   (a) reacting the mixture with a primary $C_3$- or $C_4$-alcohol in the presence of an ion exchanger in its acid form as a condensing agent to form the corresponding $C_3$- or $C_4$-alkyl tert-butyl ether by feeding the primary $C_3$- or $C_4$-alcohol and the $C_4$-hydrocarbon mixture, with or without prior mixing, to an etherification reaction zone which contains the ion exchanger;
   (b) distilling the reaction mixture obtained from the etherification reaction zone in a first distillation zone, taking off as the top product without water washing a $C_4$-hydrocarbon mixture comprising the unconverted hydrocarbons and not more than 1,000 ppm by weight of the primary $C_3$- or $C_4$-alcohol and taking off as the bottom product the resulting $C_3$- or $C_4$-alkyl tert-butyl ether, which may contain therein primary $C_3$- or $C_4$-alcohol which may have been added in excess;
   (c) feeding the bottom product to a second reaction zone, containing an acid catalyst, in which the $C_3$- or $C_4$-alkyl tert-butyl ether is decomposed at an elevated temperature to give isobutene and primary $C_3$- and $C_4$-alcohol;
   (d) feeding the mixture of isobutene and primary $C_3$- and $C_4$-alcohol produced in step (c) to a second distillation zone, taking off as the top product without a water wash isobutene containing not more than 500 ppm by weight of primary $C_3$- or $C_4$-alcohol and taking off as the bottom product the remaining primary $C_3$- or $C_4$- alcohol produced in step (c); and
   (e) Recycling the primary $C_3$- or $C_4$-alcohol which is the bottom product of step (d) to the etherification reaction zone.

2. The process of claim 1, wherein the exit temperature of the reaction mixture from the etherification reaction zone is from 25° to 65° C.

3. The process of claim 1 or 2, wherein the isobutene contained in the $C_4$- hydrocarbon mixture is converted to the extent of not less than 90% to the $C_3$- or $C_4$-alkyl tert-butyl ether in the etherification reaction.

4. The process of claim 3 wherein the etherification reaction is carried out continuously and the quotient of the volume of the etherification reaction zone and the throughput of the $C_4$-hydrocarbon mixture, containing isobutene, and the primary $C_3$- or $C_4$-alcohol is from 0.01 to 5 hours.

5. The process of claim 3 wherein the top product taken off the first distillation zone is a $C_4$-hydrocarbon mixture, comprising the unconverted hydrocarbons and containing not more than 200 ppm by weight of $C_3$- or $C_4$-alkyl tert-butyl ether or di-$C_3$-alkyl ether or di-$C_4$-alkyl ether or mixtures thereof.

6. The process of claim 3 wherein a bottom product comprising the $C_3$- and/or $C_4$-alkyl tert-butyl ether formed and containing not more than 1,000 ppm by weight of $C_4$-hydrocarbon is taken off the first distillation zone.

7. The process of claim 3 wherein the bottom product obtained from the first distillation zone and containing the $C_3$- or $C_4$-alkyl tert-butyl ether formed is employed, without separation from the primary $C_3$- or $C_4$-alcohol contained in the said bottom product, as the starting material for the decomposition stage.

8. The process of claim 3 wherein the decomposition of the $C_3$- or $C_4$-alkyl tert-butyl ether is carried out under a pressure of from 2 to 15 bars.

9. The process of claim 3 wherein, in the second distillation zone, isobutene which is not less than 99.3% by weight pure and contains not more than 100 ppm by weight of di-$C_3$-alkyl ether or di-$C_4$-alkyl ether and/or $C_3$- or $C_4$-alkyl tert-butyl ether is taken off as the top product, without interpolating a water wash.

10. The process of claim 3 wherein the content, in the primary $C_3$- or $C_4$-alcohol recycled to the etherification reaction zone, of di-$C_3$-alkyl ether or di-$C_4$-alkyl ether which may form in very small amounts as the by-product but accumulates in the recycled primary $C_3$- or $C_4$-alcohol is restricted to from 2 to 20% by weight.

11. The process of claim 3 wherein, when using isobutanol as the primary $C_4$-alcohol, a small isobutanol bleed-stream is taken off the side of the second distillation zone or form the bottom product of the second distillation zone and is dehydrated at an elevated temperature in the presence of a dehydration catalyst.

12. The process of claim 11 wherein an isobutanol part-stream containing from 3 to 40% by weight of diisobutyl ether is bled off.

* * * * *